United States Patent [19]

Pang et al.

[11] Patent Number: 5,354,765
[45] Date of Patent: Oct. 11, 1994

[54] METHOD OF TREATMENT FOR HYPERTENSION USING COMBINATION THERAPY INVOLVING EXOGENOUS CALCIUM AND DIHYDROPYRIDINE CALCIUM CHANNEL BLOCKERS

[75] Inventors: Peter K. T. Pang, 52225 Range Road 232, 205 Carriage Lane, Sherwood Park, Alberta, Canada, T8A 2A6; Richard Z. Lewanczuk, Edmonton; Christine G. Benishin, Ardrossan, both of Canada

[73] Assignee: Peter K. T. Pang

[21] Appl. No.: 918,775

[22] Filed: Jul. 27, 1992

Related U.S. Application Data

[63] Continuation of Ser. No. 460,482, Jan. 3, 1990, abandoned, which is a continuation-in-part of Ser. No. 327,450, Mar. 22, 1989, abandoned.

[51] Int. Cl.$^5$ ............... A61K 31/44; A61K 31/59; A61K 33/14; A61K 33/00
[52] U.S. Cl. ................... 514/356; 424/678; 424/715; 514/167
[58] Field of Search ............... 424/678, 715; 514/167, 514/356

[56] References Cited

U.S. PATENT DOCUMENTS

| | | | |
|---|---|---|---|
| 3,975,539 | 8/1976 | Köppe et al. | 424/304 |
| 4,621,093 | 11/1986 | Ulrich et al. | 514/355 |
| 4,703,038 | 10/1987 | Garthoff et al. | 514/19 |
| 4,837,171 | 6/1989 | Codington | 436/548 |
| 4,855,300 | 8/1989 | Nandi et al. | 514/264 |
| 4,859,665 | 8/1989 | Garthoff et al. | 514/221 |
| 4,906,647 | 3/1990 | Kouchiwa et al. | 514/356 |
| 5,047,235 | 9/1991 | Lossnitzer et al. | 424/80 |

FOREIGN PATENT DOCUMENTS

| | | |
|---|---|---|
| 1154810 | 9/1963 | Fed. Rep. of Germany . |
| WO/89/03836 | 5/1989 | PCT Int'l Appl. . |

OTHER PUBLICATIONS

Hermsmeyer et al, Calcium Channel Modulation by Dihydropyridines in Vascular Smooth Muscle, Ann. N.Y. Acd of Science, vol. 522, 1988, pp. 25–31.
Fleckenstein, The Calcium Channel of the Heart, Ann. N.Y. Acd. of Science, vol. 522, 1988, pp. 1–15.
Bukoski et al., Biochemical and Biophysical Research Communications, vol. 146, No. 3, pp. 1330–1335, 1987.
Park et al., The American Physiological Society, pp. F22–F25, 1978.
Inoue et al., Biochemical and Biophysical Research Communications, vol. 152, No. 3, pp. 1388–1394, 1988.
Baran et al., The Journal of Clinical Investigation, vol. 77, No. 5, pp. 1622–1626, May 1986.
Resnick et al., Federation of American Societies for Experimental Biology, vol. 45, No. 12, pp. 2739–2745, Nov. 1986.
Matsumura et al. The Hournal of Pharmacology, vol. 241, No. 3, pp. 1000–1005, 1987.
Kotchen et al., The American Journal of Cardiology, vol. 62, pp. 41G–46G, Oct. 5, 1988.
Park et al., The American Physiological Society, Index to vol. 240, pp. F70–F74, 1981.
Glick et al., Analytical Chemistry, vol. 60, No. 18, pp. 1982–1984; 1988.
Reichstein et al., Analytical Chemistry, vol. 60, No. 10, pp. 1069–1074, 1988.
Helmut et al, Chemical Abstracts, vol. 109, No. 143278b, p. 148, 1988.
Luft et al., Chemical Abstracts, vol. 110, No. 128289h, p. 43, 1989.
Fleckenstein et al., Zeitschrift für Kreislaufforschung, Band 56, Heft 7, pp. 717–745, 1961.

Primary Examiner—Raymond J. Henley, III
Assistant Examiner—T. J. Criares
Attorney, Agent, or Firm—Nikaido, Marmelstein, Murray & Oram

[57] ABSTRACT

Hypertensive mammals may be treated to lower mean blood pressure by administering a calcium channel blocking agent together with one or both of a calcium supplement and Vitamin D. The hypotensive effect of this combination is synergistic and the dose response is more predictable than the administration of any of these agents singly.

11 Claims, 2 Drawing Sheets

METHOD OF TREATMENT FOR HYPERTENSION USING COMBINATION THERAPY INVOLVING EXOGENOUS CALCIUM AND DIHYDROPYRIDINE CALCIUM CHANNEL BLOCKERS

This is a continuation of U.S. Pat. application Ser. No. 07/460,482, filed Jan. 3, 1990, now abandoned, which in turn is a continuation-in-part of U.S. Pat. application No. 07/327,450, filed Mar. 22, 1989 (now abandoned).

BACKGROUND OF THE INVENTION

Calcium channel blockers were identified as a method for the control of hypertension, as reported by Fleckenstein et al., *Z. Kreislaufforsch*, 56, 716 (1967), and are routinely used in the control of hypertension. Three calcium channel blockers are currently of clinical significance in the United States, verapamil, nifedipine and diltiazem. All three achieve their anti-hypertensive effect by inhibiting the entry of calcium ions into vascular smooth muscle. The ultimate effect is vasodilation.

Hypertensive hormones, such as the renin-angiotensin system (RAS), the vitamin D system, and the parathyroid hypertensive factor (PHF), are all causative factors in stimulating the increase of calcium ions in vascular smooth muscle. PHF is disclosed and described in copending patent application Ser. No. 327,450.

It has been found that calcium supplements, in dietary form, may inhibit the RAS, PHF and vitamin D systems, [Park et al., *Am. J. Physiol.*, 235, F22 (1978); Park et al., *Am. J. Physiol.*, 240, F70 (1981); Kotchen et al., *Am. J. Cardiol.*, 62, 41G (1988); Bukoski et al., *B.B.R.C.*, 147, 1330 (1987); Inoue et al., *B.B.R.C.*, 152, 1388 (1988); Baran et al., *J. Clin. Invest.*, 77, 1622 (1986); Lewanczuk et al., *Am. J. Hypertens.* (in press)] and are, therefore, beneficial in decreasing calcium uptake in vascular smooth muscle. An untoward effect of calcium supplementation is that the increased bio-availability of calcium partially negates the inhibitory effect on the endocrine system. Calcium channel blockers, by limiting the uptake of calcium in vascular smooth muscle, are beneficial, but have been found to stimulate some endocrine systems, such as the RAS system. [Kotchen et al., *Am. J. Cardiol.*, 62 41G (1988); Matsumara et al., *J. Pharmacol. Exp. Ther.*, 241, 1000 (1978); Resnick et al., *Fed. Proc.*, 45, 2739 (1986)]. Utilization of calcium channel blockers may be limited by excessive vasodilation, negative inotropy, excessive depression of the sinus nodal rate, atrial-ventricular nodal conduction disturbances and interference with non-vascular smooth muscle contraction. A combination therapy which minimizes the amount of calcium channel blocker required to achieve the desired anti-hypertensive effect is desirable.

BRIEF SUMMARY OF THE INVENTION

It now has been discovered that the use of supplemental dietary calcium and calcium channel blockers in combination is an effective method of treatment for hypertension and that the combination therapy employing both agents is more effective and predictable than the use of either agent alone. The effect is greater than the sum of the effects of both agents separately, or synergistic. Alternatively, the administration of compounds which are an effective form of Vitamin D, such as $1\alpha$, 25-dihydroxycholecalciferol ($1,25-(OH)_2D_3$), which increases intestinal calcium absorption, together with a calcium channel blocker, is a convenient treatment modality.

DETAILED DESCRIPTION OF THE INVENTION

Figure 1:
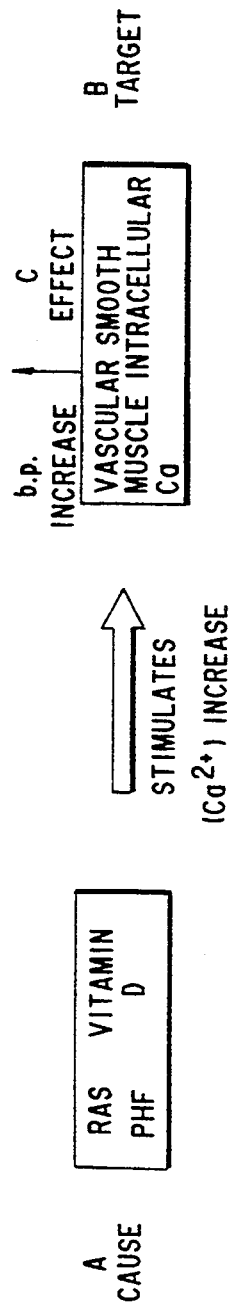
FIG. 1 illustrates the method of stimulating vascular smooth muscle contraction by systems which increase, calcium uptake.
Figure 2:
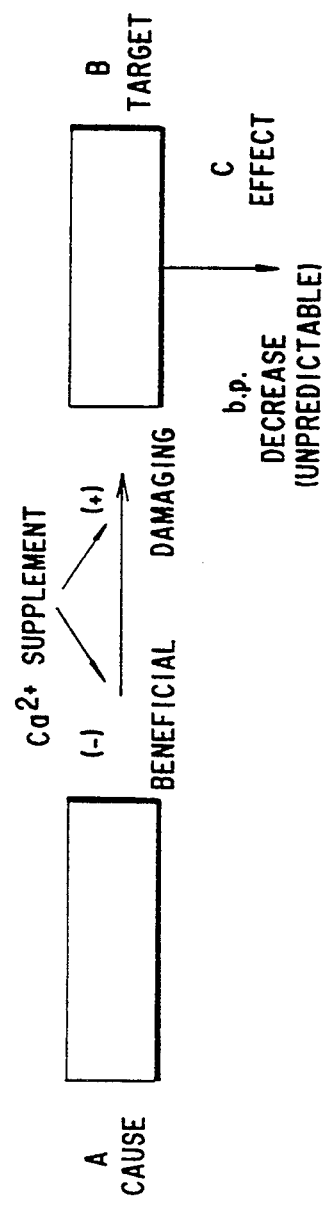
FIG. 2 illustrates the beneficial and damaging effects of calcium supplementation alone.
Figure 3:
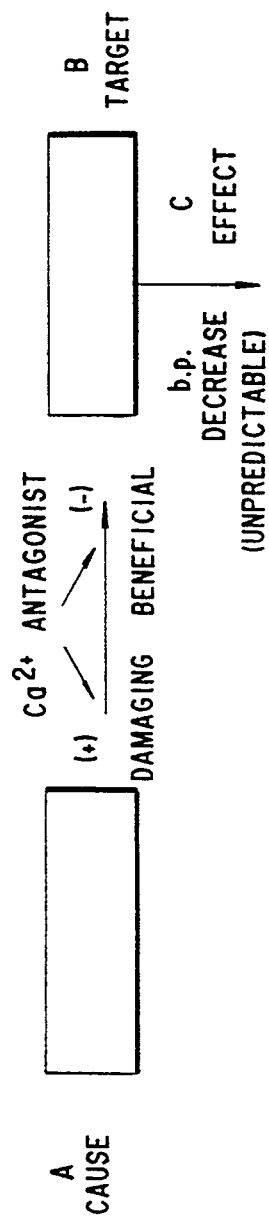
FIG. 3 illustrates the beneficial and damaging effects of calcium antagonists.
Figure 4:
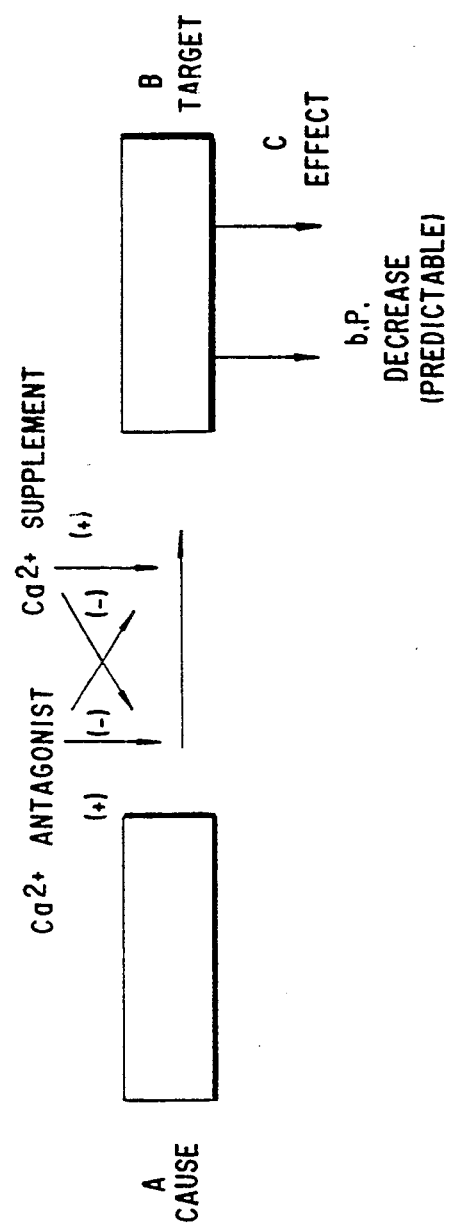
FIG. 4 illustrates the advantages of combination therapy.

We have discovered that a significant number of hypertensive mammals, including 30–40 % of humans hypertensive [Resnick et al., 13th Meeting Int'l. Soc. of Hypertens.; J. Hypertens. (in press)], have measurable levels of a parathyroid-derived hormone which increases the uptake of calcium ions in vascular tissues. This factor, which we have named parathyroid hypertensive factor, or PHF, has been isolated from spontaneously hypertensive rats (SHR) and a similar substance has been identified in human hypertensives. Application Serial No. 327,450, which is incorporated herein by reference, describes the characteristics of PHF and discloses methods for its identification.

It has been found that the production of PHF(s), as well as renin, can be inhibited by supplemental calcium and that increased levels of supplemental calcium are effective in reducing hypertension. The effects of calcium supplementation are unpredictable due to the fact that high levels of calcium in the blood may increase the bio-availability of calcium to vascular smooth muscle tissue, limiting the anti-hypertensive effect. In addition, very high levels of dietary calcium may result in undesirable and painful calcium deposits in joints and may lead to kidney stones.

The use of combination therapy involving both calcium channel blockers and dietary calcium supplementation allows the requisite lowering of blood pressure using smaller doses of the channel blocker while obtaining a greater anti-hypertensive effect. By "calcium channel blockers" is meant any pharmaceutical composition which inhibits the entry of calcium cells or inhibits the mobilization of calcium from intracellular cells. Representative examples of calcium channel blockers are dihydropyridines such as nifedipine, benzeneacetonitriles such as verapamil, and benzothiazepines such as diltiazem. As a result, not only is the therapy improved and side effects reduced, but the cost of treatment may be dramatically lowered, because the cost of calcium supplementation is much lower than the cost of available calcium channel blockers.

An effective alternative to the administration of calcium supplements, particularly when the diet contains adequate calcium, is to administer an effective form of Vitamin D, such as $1\alpha,25-(OH)_2D_3$, to increase calcium uptake in the duodenal mucosa. When calcium and/or $1\alpha,25-(OH)_2D_3$ is administered in combination with a calcium channel, it is preferable that the active components be combined in a single capsule containing appropriate unit doses of each. Patient compliance is improved when only one "medicine" is required.

The use of combination therapy involving a calcium channel blocker and calcium and/or an effective form of Vitamin D such as $1\alpha,25\text{-}(OH)_2D_3$ reduces the daily dosage of channel blocker required to less than half the dosage usually required, sometimes to as little as one-fifth of the dosage required for the channel blocker alone. The combination is compatible with other pharmaceutical compounds used for control of hypertension and angina such as angiotensin converting enzyme (ACE) inhibitors, $\beta$-adrenergic antagonists, nitrates, and diuretics.

A particular advantage of the combination of a calcium channel blocker and either or both of calcium and $1\alpha,25\text{-}(OH)_2D_3$ is the predictability of the therapy. The dose-response curve for nifedipine is not predictable in an individual patient, and a considerable period of time may be necessary to ascertain the appropriate dosage. The effect of exogenous calcium supplementation is not predictable, depending on numerous factors including rate of uptake, rate of excretion, parathyroid hormone levels and PHF levels. Somewhat surprisingly, therefore, it has been found that the combination of a calcium channel blocker and calcium supplement is not only synergistic, but that the dose response is more predictable. The time period over which a patient must be titrated is shortened and the potential for side effects is reduced because the therapeutic index is effectively raised.

The dosage of a combination pharmaceutical preparation which is used depends upon the needs of the individual patient. Typical formulations would be in capsule form containing 1/5 to ½ of the conventional dosage of a calcium channel blocker, preferably 5mg of nifedipine, with 500 mg of calcium carbonate and/or ca. 10–25 USP units (0.05 µg) of $1\alpha,25\text{-}(OH)_2D_3$.

The invention is illustrated by the following example, which is not limitative of the invention. Modification, such as the additional use of $\alpha$- and $\beta$-adrenergic blocking pharmaceuticals, diuretics, and other agents suitable for treatment of hypertension and angina by other mechanistic pathways, as would be understood by those skilled in the art, is within the scope of applicants' invention.

EXAMPLE 1

Male rats of the SHR strain, obtained from Harlan Sprague-Dawley, 12 weeks old, were divided into groups of 12 or 24, and were fed prepared diets containing 0.2%, 0.4% and 0.8% elemental calcium, respectively. Also included in the diet were 0, 50, 150 and 300 mg/kg of food of nifedipine. Distilled water was available ad lib. Feeding was continued for 8 weeks and the mean blood pressure of each animal was determined at the end of that time. The data are shown in Table 1.

From the Table, it can be seen that SHR rats on a normal diet, (0.2% dietary calcium) and which did not receive nifedipine, showed an average blood pressure of 176 mm Hg. The highest dose of nifedipine, 300 mm/kg, resulted in a decrease in blood pressure of approximately 10 mmn Hg. Using 4 times the amount of ordinary dietary calcium, the decrease in blood pressure was shown to be measurable, but small. When maximum dietary calcium and nifedipine were coadministered, blood pressure could be reduced to approximately 120 mm Hg, or a decrease of approximately 56 mm Hg, or 32% (the level found in normotensive rats).

Nifedipine in amounts of 50 or 150 mg/kg of food decreased mean blood pressure by 20mm Hg, but supplementation with 0.8% calcium reduced mean blood pressure by approximately 40 to 60 mm Hg. A combination of nifedipine and dietary supplemental calcium produced a predictable and nearly linear dose response with increased efficacy when compared to either agent alone. The data is suggestive of a synergistic relationship between the two agents.

EXAMPLE 2

A capsule containing a calcium channel blocker and a calcium supplement may be prepared using conventional techniques according to the following formulation:

| Nifedipine | 5 mg. |
|---|---|
| $CaCO_3$ | 500 mg. |
| gelatin (soft) | 1,495 mg. |

EXAMPLE 3

A capsule containing a calcium channel blocker and $1\alpha,25\text{-}(OH)_2D_3$ may be prepared using conventional techniques according to the following formulation:

| Nifedipine | 5 mg. |
|---|---|
| $1\alpha,25\text{-}(OH)_2D_3$ | 0.05 µg. |
| gelatin (soft) | 1,745 mg. |

We claim:

1. A pharmaceutical composition comprising:
   a) a blood pressure lowering effective amount of a dihydropyridine calcium channel blocker which blocks calcium channels;
   b) a calcium compound in a form capable of being absorbed in mammalian intestines, said calcium compound being present in an amount whereby the ratio by weight of elemental calcium to dihydropyridine is at least 40.

2. A pharmaceutical composition according to claim 1, wherein said dihydropyridine compound is nifedipine.

3. A pharmaceutical composition in unit dose form comprising:
   a) 10 to 50% of the minimum effective blood pressure lowering amount of a dihydropyridine calcium channel blocker which blocks calcium channels; and
   b) a calcium compound in a form capable of being absorbed in mammalian intestines and present in a blood pressure lowering effective amount.

4. A pharmaceutical composition as recited in claim 3, further comprising a pharmaceutically acceptable carrier.

5. A pharmaceutical composition as recited in claim 3, wherein said calcium compound is present in an amount of at least 200 mg of elemental calcium.

6. A pharmaceutical composition as recited in claim 1, further comprising a pharmaceutically acceptable carrier.

7. A method of treatment of hypertensive mammals comprising the coadministration of
   a) a blood pressure lowering effective amount of a dihydropyridine calcium channel blocking agent which blocks calcium channels; and
   b) a blood pressure lowering effective amount of a calcium supplement, said calcium supplement being present in an amount whereby the ratio by weight of elemental calcium to dihydropyridine is at least 40.

8. A method according to claim 7, wherein said dihydropyridine compound is nifedipine.

9. A method of treatment according to claim 7, wherein the dietary calcium is calcium carbonate.

10. A method of treatment of hypertensive mammals comprising the coadministration of
   a) 10 to 50% of the minimum effective blood pressure lowering amount of a dihydropyridine calcium channel blocking agent which blocks calcium channels; and
   b) a blood pressure lowering effective amount of a calcium supplement.

11. A method of potentiating the effect of a dihydropyridine calcium channel blocking agent which blocks calcium channels, comprising administering a potentiating effective amount of at least one source of elemental calcium together with said blocking agent.

* * * * *

UNITED STATES PATENT AND TRADEMARK OFFICE
CERTIFICATE OF CORRECTION

PATENT NO. : 5,354,765           PAGE 1 OF 2
DATED :     October 11, 1994
INVENTOR(S) : PANG et al It is certified that error appears in the above-identified patent and that said Letters Patent is hereby corrected as shown below:

In Column 1, line 29, change "copending patent application Ser. No." to --U.S. Patent No. 5,192,664--.;

In Column 1, line 30, delete "327,450."

In Column 1, line 38, change "(in press]" to --3:349-353, 1990]--.

In Column 2, line 1, change "(1,25-(OH)$_2$D$_3$)" to --(1$\alpha$,25-(OH)$_2$D$_3$)--.

In Column 2, line 8, after "increase", delete ",".

In Column 2, line 22, change "(in press)]" to --8(Suppl. 3): S101, 1990]--.

In Column 2, line 28, after "hypertensives.", delete "Application".

In Column 2, line 29, change "Serial No. 327,450" to --U.S. Patent No. 5,192,664--.

In Column 2, line 49, after "calcium", insert --into--.

In Column 2, line 50, change "cells" to --stores--.

In Column 2, line 65, after "channel" insert --blocker--.

In Column 3, line 32, change "½" to --1/2--.

In Column 3, line 58, change "300 mm" to --300 mg--.

UNITED STATES PATENT AND TRADEMARK OFFICE
CERTIFICATE OF CORRECTION

PATENT NO. : 5,354,765
DATED : October 11, 1994
INVENTOR(S) : Pang et al

It is certified that error appears in the above-indentified patent and that said Letters Patent is hereby corrected as shown below:

Column 3, line 60, change "10 mmn" to —10 mm—.

Signed and Sealed this

Sixth Day of June, 1995

Attest:

BRUCE LEHMAN

*Attesting Officer*   *Commissioner of Patents and Trademarks*